(12) United States Patent
Tyson et al.

(10) Patent No.: US 6,589,795 B2
(45) Date of Patent: Jul. 8, 2003

(54) METHOD AND DEVICE FOR DETECTING MERCURY

(75) Inventors: Julian F. Tyson, Amherst, MA (US);
Gerhard Schlemmer, Owingen (DE);
Christopher Palmer, Albany, NY (US)

(73) Assignee: PerkinElmer Bodenseewerk Zweigniederlassung der Berthold GmbH & Co. KG

( * ) Notice: Subject to any disclaimer, the term of this patent is extended or adjusted under 35 U.S.C. 154(b) by 0 days.

(21) Appl. No.: 09/801,465

(22) Filed: Mar. 8, 2001

(65) Prior Publication Data

US 2001/0034065 A1 Oct. 25, 2001

(30) Foreign Application Priority Data

Mar. 8, 2000 (DE) .......................................... 100 11 171

(51) Int. Cl.[7] .............................................. G01N 33/20
(52) U.S. Cl. .......................... 436/81; 436/171; 436/164; 436/181; 422/83; 422/88
(58) Field of Search .......................... 436/109, 81, 181, 436/171; 422/83, 88, 82.05, 91, 93; 356/36

(56) References Cited

U.S. PATENT DOCUMENTS 3,933,431 A * 1/1976 Trujillo et al. ................. 422/88
5,026,652 A * 6/1991 Huber ........................... 356/36

FOREIGN PATENT DOCUMENTS

DE 04411441 * 3/1994

OTHER PUBLICATIONS

Burguera et al. "The use of emulsions for the determination of methylmercury and inorganic mercury in fish–eggs oil by cold vapor generation in a flow injection system with atomic absorption spectrometric detection", Analyst, (1999), 124(4), 593–599.*

* cited by examiner

Primary Examiner—Jill Warden
Assistant Examiner—Yelena Gakh
(74) Attorney, Agent, or Firm—St. Onge Steward Johnston & Reens LLC

(57) ABSTRACT

The present invention relates to a method and a device for detecting mercury in a sample solution, the mercury being contained in the sample solution in cationic form and as an organic compound, by means of a detection device comprising an atomic spectroscope provided with a measuring cell which is suitable for detecting mercury gas, a noble-metal concentrator for concentrating the mercury and a control unit, the mercury being converted into the gas phase and being adapted to be concentrated by means of the noble-metal concentrator. The method according to the present invention is characterized in that the control unit controls the supply of the mercury gas to the measuring cell in such a way that, in addition to the measurement of the concentrated mercury, mercury gas of the same sample, which has not been subjected to the concentration step, is introduced in the measuring cell for the purpose of measurement. A device according to the present invention is characterized in that the supply line has provided therein a controllable valve element, which communicates with the control unit, in such a way that, under the influence of the control unit, the mercury gas of the same sample solution can selectively be introduced from the concentrator or directly from the gas phase area into the measuring cell. A further device according to the present invention is characterized in that it comprises a second measuring cell which is adapted to have supplied thereto mercury gas directly from the gas phase area under the control of the control unit.

15 Claims, 3 Drawing Sheets

METHOD AND DEVICE FOR DETECTING MERCURY

FIELD OF THE INVENTION

The present invention relates to a method and a device for detecting mercury in a sample solution containing the mercury in cationic form and as an organic compound, by means of a detection device comprising an atomic spectroscope provided with a measuring cell which is suitable for detecting mercury gas, a noble-metal concentrator for concentrating the mercury and a control unit, the mercury being converted into the gas phase and being adapted to be concentrated by means of the noble-metal concentrator.

BACKGROUND OF THE INVENTION

Mercury is one of the elements having a toxic effect on human beings and animals in a very low concentration. It is therefore necessary to detect mercury concentrations even in very small doses. In addition to the total mercury concentration, especially also the chemical species in which the mercury appears in the sample to be tested are of importance. In this respect, methyl mercury is regarded as one of the most frequently appearing species, having, in addition, an extremely toxic effect.

In conventional methods and devices mercury is detected e.g. by means of the optical atomic spectrometry in the form of atomic absorption spectrometry, atomic fluorescence spectrometry, atomic emission spectrometry or mass spectrometry. In the case of these methods the mercury contained in cationic form or as an organomercury compound in a solution to be tested is determined e.g. by the so-called cold-vapour technique. For this purpose, the mercury contained in the solution is converted by reaction into an atomic gas or vapour, whereupon it is possible to carry out mercury detection by one of the above-mentioned methods in the field of measurement technology.

In order to increase the power of detection, other components in the solution can be eliminated. The sensitivity in the detection process can be increased still further by conducting the mercury gas produced first over a net of noble-metal alloys and by concentrating it then by amalgamation. Subsequently, the mercury adhering to the net is released in the form of mercury gas by heating the net, whereupon it is subjected to the measurement.

By means of these methods it is possible to determine the total mercury content; for a separate determination of e.g. methyl mercury, a previous separation into species will, however, be necessary. This separation normally takes place in a chromatographic method or via cooled condensation traps. This, however, necessitates a separation unit and a detection unit as well as essential additional efforts for preparing the sample so as to carry out this separate determination of the methyl mercury content and of the total mercury content.

Furthermore, a method is imaginable which utilizes the fact that cationic mercury can be converted into the vapour or gas phase with mild reducing agents, whereas certain organomercury compounds can only be converted into the vapour or gas phase with comparatively strong reducing agents. It is true that this method offers an advantage in comparison with the above-mentioned method as far as the simplicity of sample preparation is concerned, but for successively determining the total mercury content and the methyl mercury content two separate reaction units have to be used, since the two reducing agents mutually influence one another. In addition, it turns out in practice that, due to the use of two reducing agents and of two reaction units, the experimental parameters cannot be controlled in a way which permits the mercury content to be determined with the necessary accuracy and reproducibility.

It is therefore an object of the present invention to provide a method and a device which permit by means of a simple treatment of the sample a reliable determination of the total mercury content and of the mercury content in the form of an organic compound.

SUMMARY OF THE INVENTION

According to the present invention, this object is achieved by providing a method of the type mentioned at the beginning in the case of which the control unit controls the supply of the mercury gas to the measuring cell in such a way that, in addition to the measurement of the concentrated mercury, mercury gas of the same sample, which has not been subjected to the concentration step, is introduced in the measuring cell for the purpose of measurement.

The present invention is based on the inventors' finding that when the mercury is converted into the gas phase, e.g. by reduction with sodium hydridoborate, this has not only the effect that cationic mercury is converted into the gas phase, but also that organomercury, such as methyl mercury, is also released as a gaseous compound. The gaseous mercury developing from the cationic mercury can directly be detected in a measuring cell. The gaseous compound developing from the methyl mercury does, however, not cause any specific atomic absorption or atomic fluorescence during this measurement. It follows that, even if the sample solution is treated such that not only gaseous mercury develops from the cationic or inorganic mercury but that a gaseous compound of the organomercury (methyl mercury) develops as well, a measurement in the measuring cell will still exclusively indicate the content of cationic mercury in the sample.

The gaseous compounds produced can be collected on the concentrator, e.g. a noble-metal net or sand coated with noble metal, and amalgamated. Under the catalytic influence of the noble metal, the organic gaseous mercury compounds will decompose. When the mercury has been released from the concentrator and subsequently introduced in the measuring cell, the sum of inorganic (cationic) and organic mercury will therefore be detected. This permits a determination of the content of organic mercury and of the total mercury content by means of two successive measurement steps; a simple sample preparation will suffice for this purpose.

According to an advantageous embodiment, the mercury contained in the sample solution is converted into the gas phase by reduction. Hence, known devices can be used for reducing the sample in the method according to the present invention, whereby the expenditure for the devices required will be reduced.

According to an advantageous further development of the present invention, the sample containing the mercury is reduced with sodium hydridoborate.

In the course of the experiments carried out by the inventors, it turned out that especially the gaseous mercury compounds obtained by a reduction with sodium hydridoborate permit a reliable determination of the inorganic or cationic as well as of the total mercury content.

According to another advantageous further development, the mercury gas will be introduced into the measuring cell without having been subjected to the concentration step, if the control unit has detected that a predefined threshold value has been exceeded in the preceding measurement of the concentrated mercury gas supplied from the concentrator.

Due to the fact that a threshold value is predetermined and that this threshold value is automatically supervised, a swift measurement is guaranteed, since only the second measurement step for determining the inorganic mercury content will be carried out, if an admissible total mercury content has been exceeded.

According to an advantageous embodiment, the control unit determines an overall result on the basis of the measurement results of the two measurements.

In this way it is, on the one hand, possible to automatically determine the total mercury content as well as the amount of inorganic mercury in a sample, and, on the other hand, the content of organic mercury compounds can be determined automatically with due regard to the two measurement results.

The method can be used in an advantageous manner when the organic mercury compound contains methyl mercury.

The method according to the present invention thus permits a simple preparation of a sample containing mercury and the simultaneous determination of the amount of extremely toxic methyl mercury as well as of the total mercury content.

The present invention also provides a device for detecting mercury in a solution, comprising a gas phase area in which the mercury in the solution can be converted into the gas phase, a concentrator for concentrating the mercury, an atomic spectroscope provided with a measuring cell which is implemented such that it is suitable for detecting mercury, a supply line which serves to introduce the mercury gas into the measuring cell, and a control unit communicating with the measuring cell, said device being characterized in that the supply line has provided therein a controllable valve element, which communicates with the control unit, in such a way that, in dependence upon said control unit, the mercury gas of the same sample solution can be introduced from the gas phase area into the measuring cell selectively with or without the concentrator.

It follows that this device according to the present invention is particularly suitable for executing the method according to the present invention, since the valve element permits a controlled supply of a sample gas selectively from the concentrator or from the gas phase area.

The present invention additionally relates to a device for detecting mercury in a solution, comprising a gas phase area in which the mercury in the solution can be converted into the gas phase, a concentrator for concentrating the mercury, an atomic spectroscope provided with a first measuring cell which is implemented such that it is suitable for detecting mercury gas from the concentrator, a supply line which serves to introduce the mercury gas into the first measuring cell, and a control unit communicating with the first measuring cell, said device being characterized by the following features according to the present invention: that the device comprises a second measuring cell which communicates with the control unit and which, under the control of said control unit, is adapted to have supplied thereto mercury gas directly from the gas phase area excluding the concentrator.

The provision of a second measuring cell, which is adapted to have supplied thereto mercury gas directly from the gas phase area, is particularly suitable for the above-mentioned method according to the present invention; an increased measurement speed can be achieved in view of the fact that reference and calibration measurements, respectively, can be carried out in the second measuring cell e.g. during the measurement taking place in the first measuring cell so that a high measurement accuracy can still be achieved in the case of high measurement speeds.

According to an advantageous embodiment, the gas phase area comprises a reduction area in which the mercury can be converted into the gas phase by reduction.

This permits the use of known reduction devices in the device according to the present invention, whereby an economy-priced overall solution will be obtained.

According to an advantageous embodiment, the control unit is implemented such that it is adapted to form on the basis of the measurement of the mercury content of the gas supplied from the concentrator and on the basis of the measurement of the amount of mercury supplied from the gas phase area a total value resulting from both measurements.

When this total value resulting from both measurement processes is being determined, the different pretreatments of the mercury gas, when said mercury gas is fed from the concentrator and directly from the gas phase area, respectively, are taken into consideration. Furthermore, the control unit can constantly cause the execution of a reference measurement in the measuring cell or measuring cells so as to incorporate a shift of experimental parameters in the evaluation and combination of the individual measurements.

A further embodiment is obtained in combination with the atomic absorption spectrometer device disclosed in DE 44 11 441 in which the measuring cell comprises at least two chambers which are adapted to be connected to one another and through which a light beam can be passed, the light absorption paths of these chambers being in a certain ratio to each other.

On the basis of the subdivision of the measuring cell into at least two connectable, separate chambers it is possible to provide different light absorption paths for the sample substance which is to be examined with regard to its mercury content. The chamber having the longer light absorption path may serve to detect the mercury which is directly supplied from the gas phase area into the measuring cell, so as to achieve a higher sensitivity in comparison with the sample supplied from the concentrator into the measuring cell.

Furthermore, it will also be advantageous when, by means of a division into separate chambers or by a suitable selection of the length and, consequently, of the absorption length, the second measuring cell is adapted to the behaviour of the first measuring cell into which the mercury is fed from the concentrator. This measure permits a substantial increase in the accuracy of the measurement and of the total result.

According to an advantageous embodiment, the chambers in the measuring cells are adapted to be connected by switching valves which are controllable by the control unit. An automatic light absorption length of the spectrometer, which is adapted to the respective measurement conditions, can be adjusted in this way.

Further advantageous embodiments are disclosed in the subclaims.

In the following, the present invention will be explained on the basis of preferred embodiments with reference to the drawings, in which:

BRIEF DESCRIPTION FO THE DRAWINGS

Figure 1:
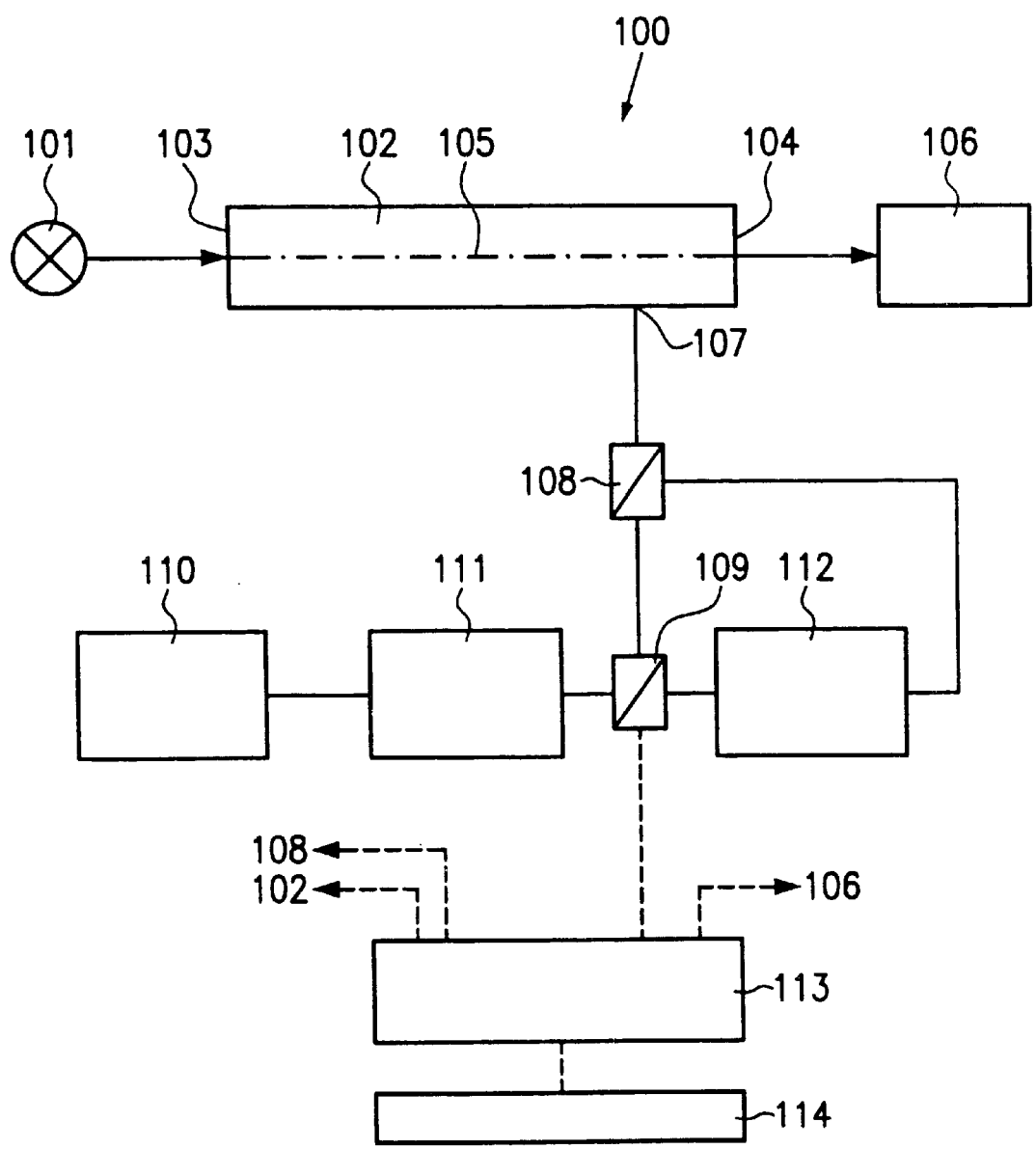
FIG. 1 shows a schematic representation of an embodiment of the present invention used for detecting mercury.

FIG. 1 shows an embodiment of a device 100 according to the present invention used for detecting mercury. The device 100 comprises a light source 101, a measuring cell 102 and a light detection device 106 which are arranged along an optical axis 105. The light source 101, the measuring cell 102 and the light detection device 106 form an atomic absorption spectrometer. The light source 101 comprises e.g. a mercury low-pressure discharge lamp generating an intensive radiation at the emission and absorption lines of the mercury. The light detection device 106 is preferably an electrooptical transducer which converts radiant power impinging on a surface of said electrooptical transducer into an electric signal. Devices which proved to be particularly advantageous for this purpose are photodiodes with a coated photocathode, a CsSe photocathode being e.g. provided for measuring the intensity of the emission line 184.9 nm and a CsTe photocathode being e.g. provided for measuring the emission line 253.7 nm.

The measuring cell 102 comprises an elongate, tubular cell which is arranged along the optical axis 105. In the longitudinal direction the measuring cell 102 is delimited by windows 103, 104 which are transparent to the absorption wavelength. A side wall of the measuring cell 102 is provided with a radial gas supply 107 which is connected to a controllable three-way valve 108 on the other side thereof. The input ports of the three-way valve 108 have respectively coupled thereto supply lines from a mercury concentrator 112 and of a further three-way valve 109. The second outlet of the three-way valve 109 is connected to the concentrator 112. The inlet side of the three-way valve 109 is connected to a reduction area 111 which, in turn, is in fluid communication with a sample container 110 containing the mercury solution in a concentrated form.

A control unit 113, which may e.g. be implemented as a microprocessor control or as a personal computer with a suitable peripheral equipment, is electrically connected to the three-way valves 108 and 109 as well as to the light detection device 106. The control unit 113 additionally comprises a display/output element 114 in which information can be represented visually, acoustically, in printed form or in an arbitrary suitable way.

Furthermore, reference should be made to the fact that any other suitable valve element can be used instead of a three-way valve. It is also possible to equip the measuring cell with two supply lines from the reduction area and from the concentrator, respectively, which are provided with suitable switching valves, so that the control unit can selectively supply sample gas from said reduction area or from said concentrator to the measuring cell.

DETAILED DESCRIPTION OF THE INVENTION

For operating the device 100 the sample container 110 has supplied thereto a solution of the sample to be tested. The solution to be tested can previously be separated into species by means of suitable known devices, such as chromatographic columns or cooled condensation traps. The solution to be tested is then supplied to the reduction area 111 in which mercury which may be contained in the solution is reduced by means of a reducing agent, in this case sodium hydridoborate. During the reduction gaseous mercury as well as a gaseous compound containing methyl mercury are formed, already at room temperature, from the cationic mercury in the solution to be tested. The conversion into the gas phase can also be carried out in a gas phase area without any reduction area, e.g. by heating the solution.

During the continued measuring operation, the control unit 113 controls the three-way valve 109 in such a way that the resultant gas is transferred to the concentrator 112. The concentrator 112 essentially comprises a noble metal which, for enlarging the surface, is vapour deposited in the form of a net or e.g. on sand and to the surface of which the gaseous mercury becomes attached. In the course of this process, the gaseous methyl mercury compound decomposes under the catalytic influence of the noble metal and after the heating of the noble metal a concentrated mercury gas is formed, which contains both the mercury originally existing in organic compounds and the inorganic mercury. The concentrated mercury gas is transferred via a fluid line to the three-way valve 108 which is controlled by the control unit 113 in such a way that it communicates with the measuring cell 102 via the connecting branch 107. Subsequently, an absorption measurement is carried out which, on the basis of the explanation given hereinbefore, determines the total mercury content in the sample, since the organomercury compounds and in particular the methyl mercury decompose during the concentration and are converted into a form which is detectable by atomic absorption. After having passed through the sample gas, the signal of the light detection device 106 is received by the control unit 113 and evaluated. If a predefined threshold value of the total mercury content is exceeded, it will be advantageous to switch, after having removed the sample gas from the measuring cell 102 after the measurement, the three-way valve 109 by means of the control unit 113 in such a way that the sample gas will be transferred directly from the reduction area 111 into the measuring cell 102 via the three-way valve 108 that has been switched in a suitable manner as well. In an additional measurement the amount of cationic or inorganic mercury is determined, since in particular the methyl mercury, which is also contained in a gaseous compound, does not cause any specific atomic absorption or atomic fluorescence. Hence, it is exclusively the content of cationic mercury which is determined in this measurement. The control unit can therefore determine the amount of methyl mercury in the sample on the basis of the previously determined total mercury content of the sample. It goes without saying that the determination of the methyl mercury content and of the total mercury content can also be carried out independently of a predetermined threshold value in the case of each measurement.

Figure 2:
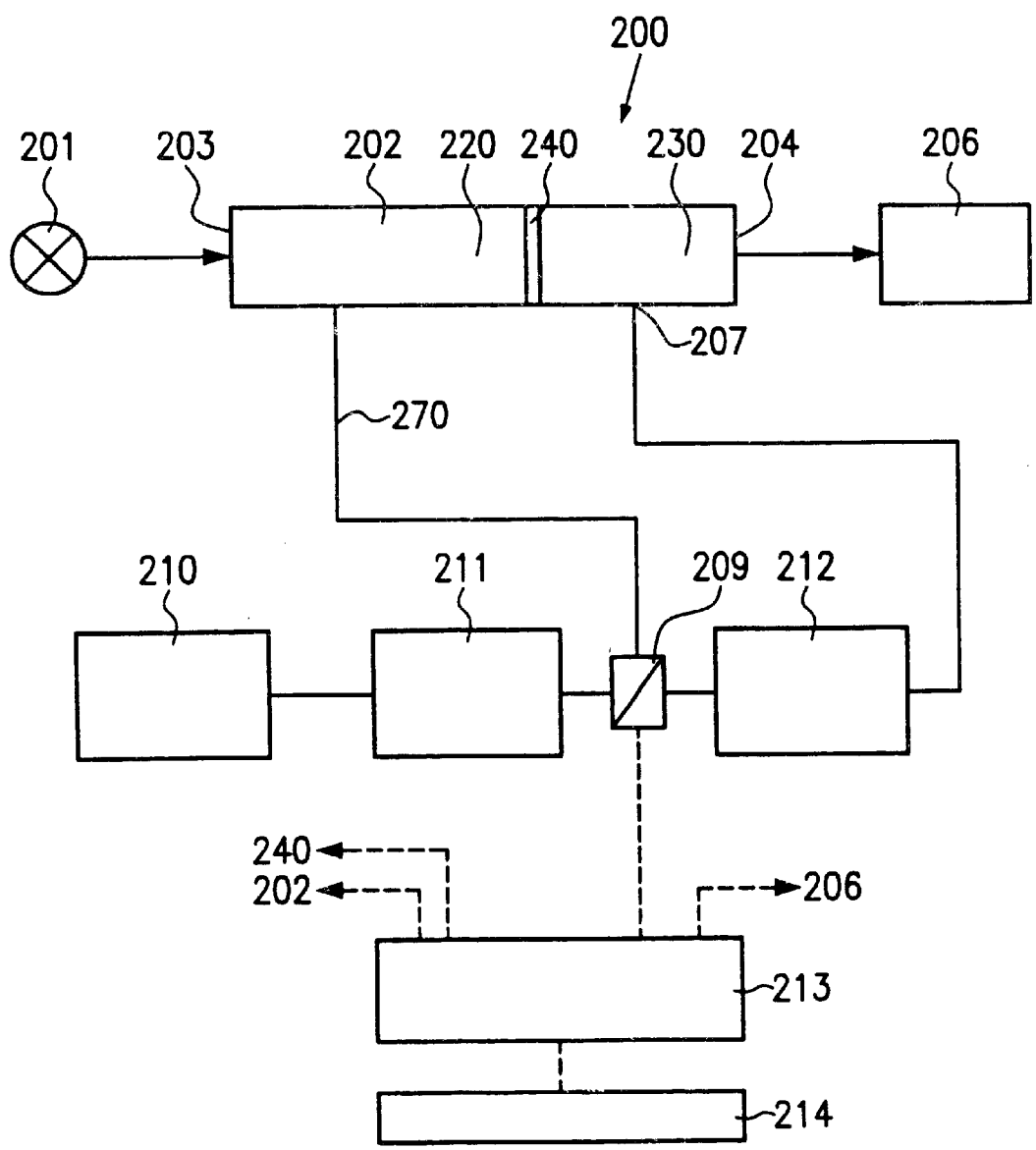
FIG. 2 shows a schematic representation of a further embodiment of the device comprising a measuring cell with two separate chambers.

FIG. 2 shows a further embodiment of a device 200 for detecting mercury. Components which are identical with the components that have been explained with respect to FIG. 1 are designated by the same reference numerals in this FIG. 2 and the explanation of these components is omitted. Only the leading "1" is replaced by a "2" in this embodiment. The device 200 differs from the device 100 essentially insofar as the measuring cell 202 comprises two separate chambers 220 and 230. The chambers 220 and 230 are separated by a switching valve 240 such that a connection can be established between them. In this embodiment the chamber 220, which has the same diameter as the chamber 230, is longer and has therefore a longer optical absorption path. Furthermore, the chamber 220 is directly connected to the three-way valve 209, whereas the chamber 230 is directly connected to the concentrator 212 via a supply line.

During the measuring operation the control unit 213 controls the three-way valve 209 in such a way that the mercury gas from the concentrator 212 is introduced in the chamber 230. The switching valve 240 is controlled by the control unit 213 in such a way that no connection to chamber 220 exists. During the subsequent measurement the total mercury content in the sample is again determined in the manner described hereinbefore. In an additional measurement, which is again initiated by the control unit 213 e.g. in response to an exceeded threshold value, the sample gas is removed from chamber 203 and the three-way valve 209 is then controlled in such a way that the sample gas is conducted from the reduction area 211 directly into the chamber 220. The switching valve 240 can selectively be controlled in such a way that either the full absorption length of chambers 220 and 230 or only the absorption length of chamber 220 is available. It follows that an adaptation of the sensitivity in the case of both measurements can be achieved by suitably predetermining the lengths of the chambers 220 and 230. On the basis of the measurement of the sample gas supplied directly from the reduction area 211, the amount of cationic mercury can be determined. On the basis of both measured values, the total content of mercury as well as the content of methyl mercury in the sample can again be determined.

Figure 3:
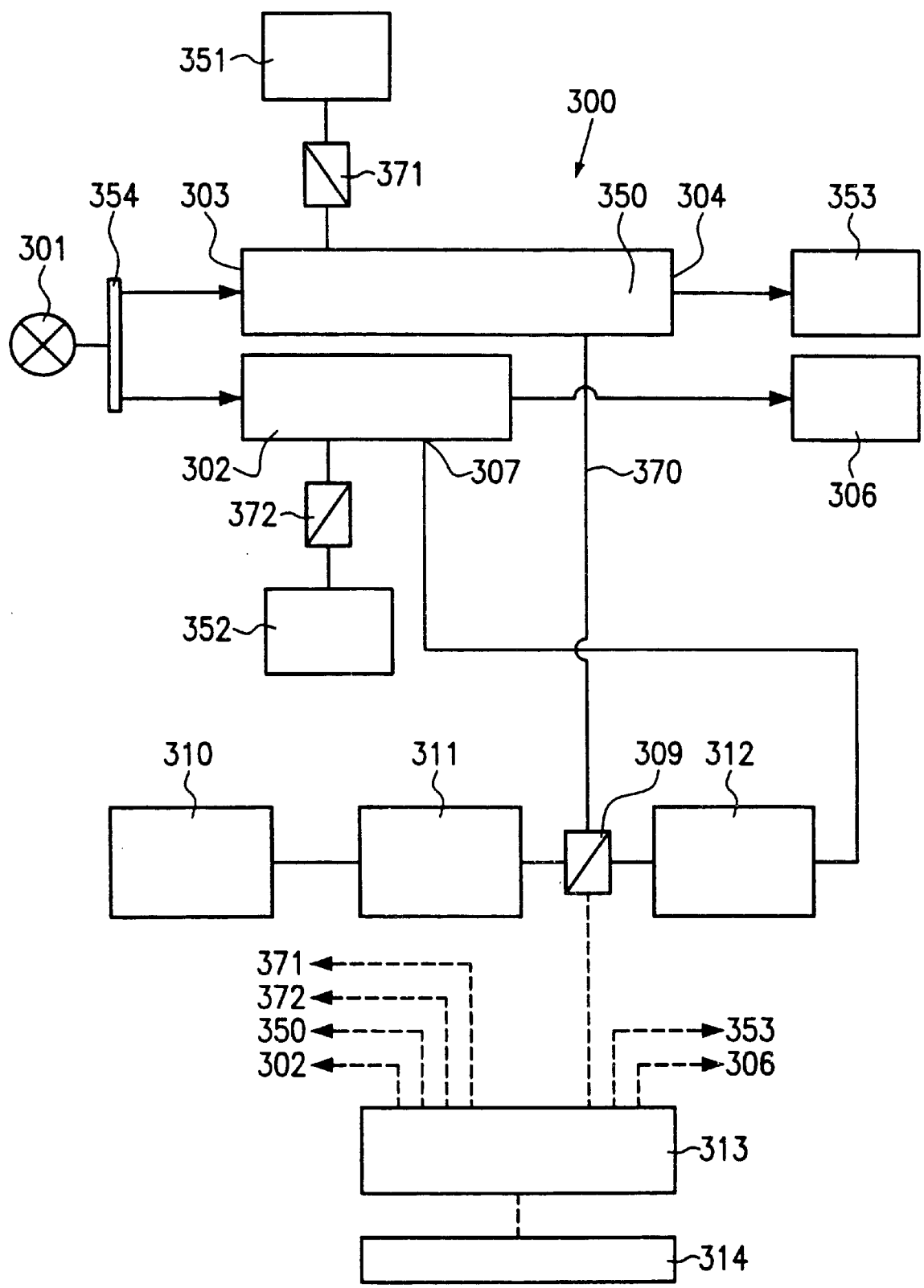
FIG. 3 shows a schematic representation of a further embodiment of the device according to the present invention comprising a second measuring cell.

FIG. 3 shows a further embodiment of a device 300 for detecting mercury. Elements which are identical with the embodiment according to FIG. 1 are again shown with the same reference numerals with the exception of a leading "3" instead of a "1". The device 300 is provided with a beam-splitting element 354 which is able to divide the light of the light source 301 into two sub-beams. In addition, the device 300 comprises a second measuring cell 350 as well as a second light detection device 353. The second measuring cell communicates with the three-way valve 309 via a fluid connection 370, whereas the measuring cell 302 is connected to the connecting branch 307 of the concentrator 312 via a suitable line. In this embodiment the second measuring cell 350 has an absorption length which exceeds that of the measuring cell 302. Both measuring cells may, however, also have the same length or one or both measuring cells may be implemented such that it is/they are subdivided into chambers, as has been explained with respect to FIG. 2. Furthermore, the second measuring cell 350 is connected to a reference container 351, whereby a reference sample can be introduced into the measuring cell via a controllable valve 371. A reference container 352 for the measuring cell 302 with a controllable valve 372 is provided in a corresponding manner.

The measurement of the mercury content of the sample can be carried out in a manner which is similar to the measurement which has already been explained with respect to FIGS. 1 and 2. Furthermore, due to the fact that a second measuring cell is provided, this embodiment offers the possibility of executing a reference measurement in the second measuring cell while a measurement is being carried out in the first measuring cell so that, on the whole, a reduced measurement time in combination with an increased accuracy will be obtained. For this purpose, the control unit 113 controls the respective valve elements 371, 372 such that reference samples are supplied from the containers 351 and 352 in conformity with the sequence of measuring steps. Furthermore, the control unit 113 is capable of processing simultaneously the signals of the light detection devices 353 and 306 and to incorporate these signals into the determination of the measurement result.

In the above described embodiments the method according to the present invention and the devices according to the present invention have been described in connection with atomic absorption spectroscopy. It goes without saying that the present invention can be implemented in a method and in a device, respectively, in which detection is executed by means of atomic fluorescence. The light source and the light detection device remain unchanged in this case, since the detection carried out is also a wavelength-specific detection. It will only be necessary to adapt the structural design of the measuring cell and the arrangement of the light detection device in such a way that the detection can take place at a certain angle to the incoming light.

What is claimed is:

1. A method of detecting mercury in a sample solution containing the mercury in inorganic form and as an organic compounds by means of a detection device comprising
    an atomic spectroscope provided with a measuring cell adapted to detect mercury gas,
    a noble-metal concentrator for concentrating the mercury, and
    a control unit,
the method comprising:
    converting the inorganic and organic mercury into the gas phase by reduction, thereby creating resultant gaseous mercury;
    supplying a first volume of the resultant gaseous mercury to the nobel-metal concentrator;
    concentrating the first volume of resultant gaseous mercury, thereby creating concentrated gaseous mercury
    supplying the concentrated gaseous mercury to the measuring cell; subjecting the concentrated gaseous mercury to a measurement;
    supplying a second volume of the resultant gaseous mercury to the measuring cell for performing a measurement; wherein
        the control unit controls the supply of the concentrated gaseous mercury and the second volume of the resultant gaseous mercury.

2. A method according to claim 1, wherein the mercury contained in the sample solution is converted into the gas phase by reduction.

3. A method according to claim 2, further comprising reducing the sample containing the mercury by means of sodium hydridoborate.

4. A method according to claim 1, wherein the control unit determines an overall result on the basis of the measurements of the concentrated gaseous mercury and the second volume of unconcentrated gaseous mercury.

5. A method according to claim 1, wherein the organic mercury compound comprises methyl mercury.

6. A method according to claim 5, wherein the control unit determines the amount of methyl mercury on the basis of the measurement of the second volume of unconcentrated gaseous mercury and on the basis of the measurement of the concentrated gaseous mercury.

7. A device for detecting mercury in a solution comprising
    an atomic spectroscope provided with a measuring cell adapted to detect mercury;
    a supply line connected to the measuring cell for introducing mercury gas thereinto;
    a controllable valve element connected to the supply line;
    a gas phase area connected to the controllable valve element, in which area the mercury in the solution can be converted into the gas phase;
    a concentrator connected to the controllable valve element for concentrating the mercury gas; and a control unit connected to the controllable valve element to select mercury gas from either the gas phase area or the concentrator for introduction into the measuring cell.

8. A device for detecting mercury in a solution, comprising;
   an atomic spectroscope provided with a first measuring cell adapted to detect mercury,
   a second measuring cell adapted to detect mercury,
   a first supply line connected to the first measuring cell,
   a second supply line connected to the second measuring cell,
   a controllable valve element connected to the first supply line and the second supply line,
   a gas phase area connected to the controllable valve element, in which area the mercury in the solution can be converted into the gas phase; and
   a concentrator connected to the controllable valve element and the first supply line for concentrating the mercury gas; and
   a control unit connected to the controllable valve element.

9. A device for detecting mercury in a solution according to claim 7, wherein the gas phase area comprises a reduction area in which the mercury can be converted into the gas phase by reduction.

10. A device for detecting mercury in a solution according to claim 9, wherein the reduction area is adapted to have supplied thereto a reducing agent, in particular sodium hydridoborate.

11. A device for detecting mercury in a solution according to claim 7, wherein the control unit is adapted to determine a total value for the total amount of mercury on the basis of the measurement of the mercury content of the mercury gas supplied from the concentrator and on the basis of the measurement of the mercury amount supplied from the gas phase area.

12. A device for detecting mercury in a solution according to claim 8, wherein an effective absorption length of the second measuring cell exceeds an effective absorption length of the measuring cell.

13. A device for detecting mercury in a solution according to claim 7, wherein the measuring cell comprises at least two optically coupled chambers which are adapted to be connected to one another.

14. A device for detecting mercury in a solution according to claim 13, wherein the measuring cell comprises a switching element by means of which the at least two chambers can be connected in a manner which is controllable by the control unit.

15. A method according to claim 4, wherein the step of determining an overall result includes determining the total mercury content of the sample, further comprising the step of determining whether a predefined threshold value of the total mercury content has been exceeded.

* * * * *